US006432430B1

United States Patent
Fitzjarrell

(12) United States Patent
(10) Patent No.: US 6,432,430 B1
(45) Date of Patent: Aug. 13, 2002

(54) EXFOLIATING SCRUB WITH NIACINAMIDE

(76) Inventor: Edwin Fitzjarrell, P.O. Box 3600, Sisters, OR (US) 97759

( * ) Notice: Subject to any disclaimer, the term of this patent is extended or adjusted under 35 U.S.C. 154(b) by 0 days.

(21) Appl. No.: 09/715,498

(22) Filed: Nov. 17, 2000

(51) Int. Cl.$^7$ .............................. A61K 7/48; A61K 7/50; A61K 7/06
(52) U.S. Cl. ...................... 424/402; 424/401; 424/70.1; 424/78.03; 424/78.05; 424/78.06; 424/78.07
(58) Field of Search ................................. 424/402, 401, 424/70.1, 78.03, 78.05, 78.07, 78.06

(56) References Cited

U.S. PATENT DOCUMENTS

| | | | |
|---|---|---|---|
| 4,505,896 A | 3/1985 | Bernstein | |
| 4,593,046 A | 6/1986 | Gruber | |
| 4,619,829 A | 10/1986 | Motschan | |
| 4,725,609 A | 2/1988 | Kull, Jr. et al. | |
| 4,743,442 A | 5/1988 | Raaf et al. | |
| 4,900,550 A | 2/1990 | Lowry | |
| 5,266,318 A | 11/1993 | Taylor-McCord | |
| 5,449,512 A | 9/1995 | Simmons | |
| 5,496,827 A | 3/1996 | Patrick | |
| 5,520,919 A | 5/1996 | Lerner | |
| 5,520,991 A | 5/1996 | Eustatiu | |
| 5,527,530 A | 6/1996 | Simmons et al. | |
| 5,556,887 A | 9/1996 | Lerner | |
| 5,705,166 A | * 1/1998 | Arve | ........................... 424/401 |
| 5,759,559 A | 6/1998 | Fitzjarrell | |
| 5,939,082 A | 8/1999 | Oblong et al. | |
| 5,939,085 A | * 8/1999 | Jacobs et al. | ................ 424/401 |
| 5,968,528 A | 10/1999 | Deckner et al. | |
| 5,980,921 A | 11/1999 | Biedermann et al. | |
| 5,989,523 A | 11/1999 | Fitzjarrell | |
| 5,989,528 A | 11/1999 | Tanner et al. | |
| 5,997,890 A | 12/1999 | Sine et al. | |
| 6,093,408 A | 7/2000 | Hasenoehrl et al. | |
| 6,183,761 B1 | 2/2001 | Bissett et al. | |
| 6,217,888 B1 | * 4/2001 | Oblong et al. | ............... 424/401 |
| 6,218,348 B1 | * 4/2001 | Aronson et al. | ............ 510/153 |
| 6,238,678 B1 | * 5/2001 | Oblong et al. | ............... 424/401 |

FOREIGN PATENT DOCUMENTS

GB 964444 7/1964

OTHER PUBLICATIONS

Brul S., Coote P. Preservative agents in foods. Mode of action and microbial resistance mechanisms. International Journal of Food Microbiology. Sep. 15, 1999, 50 (1–2):1–17.*

Jablonska, M.D., Treatment of Acne Vulgaris and Rosacea, letter to the editor, Arch. Dermatology, vol. 111, Jul. 1975, p. 929.

Comaish, Topically Applied Niacinamide in Isoniazid–Induced Pellagra, Arch. Dermatology, vol. 112, Jan. 1976, pp. 70–72.

Shalita, Alan, R.; et al., Topical Nicotinamide Compared With Clindamycin Gel in the Treatment of Inflammatory Acne Vulgaris, Int. J. Dermatol., 1995, V. 34, pp. 434–437.

Syed, T.A., et al., Management of Psoriasis with Aloe vera Extract in a Hydrophyllic Cream: a placebo–controlled, double blind study. Trop. Med. Int. Health, Aug. 1996, 1(4), pp. 505–509.

* cited by examiner

Primary Examiner—Thurman K. Page
Assistant Examiner—Rachel M. Bennett
(74) Attorney, Agent, or Firm—Ipsolon LLP

(57) ABSTRACT

An exfoliating scrub contains in a mild cream or gel base a therapeutically effective concentration of niacinamide and an abrasive exfoliating agent, preferably powdered walnut shells. The scrub is applied topically to areas of the skin that are to be treated and is massaged into the skin. The scrub is thereafter removed. The scrub contains niacinamide in an amount between about 1 and 20% by weight.

6 Claims, No Drawings

EXFOLIATING SCRUB WITH NIACINAMIDE

FIELD OF THE INVENTION

This invention relates to a dermatological preparation for use in the treatment of skin disorders and the like. More specifically, the invention relates to an exfoliating scrub that contains therapeutically effective amounts of niacinamide and exfoliating agents. The scrub is useful in the treatment of blemishes and inflammations caused by acne and similar conditions.

BACKGROUND AND SUMMARY OF THE INVENTION

Acne is a skin condition that occurs most frequently among adolescents and is characterized by an excessive secretion of sebum or dermal oil from the sebaceous glands. Sebum normally reaches the skin surface through the duct of a hair follicle and a connected pore. During adolescence and at other times, the amount of sebum secreted by the pilosebaceous system may increase to the point where the follicular ducts and pores are obstructed, causing sebum to accumulate under the skin and producing a solidification of the sebum called a comedome. This in turn results in hyperkeratinization of the follicular opening, which can cause complete obstruction of the duct.

The dermatological manifestations of the obstruction of follicular ducts may include papules, pustules and cysts that are often associated with bacteria and secondary infection. These indications are generally referred to as acne. The blemishes that result from acne can range from mild skin irritation to severely disfiguring scarring in sever cases.

There are many treatments available for acne. For example, mild cases can be treated with dietary changes and careful washing with lotions containing benzoyl peroxide, and topical creams containing salicylic acid. Other treatment regimens, such as those suggested by Lerner in U.S. Pat. No. 5,556,887 recommend the use of vitamin A palmitate applied topically. There are many other useful treatment regimens for acne. The particular treatment used by an individual depends of course on many factors, including the severity of the condition.

One particularly useful therapeutic agent in the treatment of acne is niacinamide and several U.S. patents and other references disclose formulations for its effective use in treating acne and other dermatological disorders. Niacinamide is known to be beneficial in the treatment of dermatological lesions for many reasons, including its known anti-inflammatory properties and the fact that it does not induce bacterial resistance. One example of a reference that discloses the use of niacinamide in the treatment of acne is U.S. Pat. No. 4,505,896. In the '896 patent, niacinamide (also commonly referred to as nicotinamide) is administered either orally or topically. The formulations disclosed in the '896 patent include various other compounds known to be effective in the treatment of acne, including sulfur, salicylic acid, benzoyl peroxide and vitamin A.

The topical treatment regimen described in the '896 follows the accepted traditional methods of using niacinamide. That is, the niacinamide is applied topically and is not removed, for instance, by washing. Other references use the same basic approach. For example, in their study entitled *Topical Nictotinamide Compared With Clindamycin Gel in the Treatment of Inflammatory Acne Vulgaris*, Shalita and Smith had patients apply a topical gel containing 4% niacinamide (nicotinamide) twice daily. (Int. J. Dermatol., 1995, V. 34, pp. 434–437.) The gel was not washed off. Likewise, in a study published in the United Kingdom in 1976, Comaish et al. describe the topical application of a cream containing 1% niacinamide. (*Arch. Dermatology*, Vol. 112, January 1976, pages 70–72.) Again, the cream was not removed.

As effective as the topical application of niacinamide is known to be, there are adverse side effects associated with it, including in some patients stinging, dryness and other discomfort. Applicant recognized these side effects and was granted U.S. Pat. No. 5,989,523, which is yet another example of a topical spray that contains niacinamide as an active ingredient. Like the references discussed above, this patent teaches that treatment of acne with topically applied niacinamide-containing products requires that the product be left on the skin for a significant period of time in order for the niacinamide to be therapeutically effective. Indeed, the topical spray disclosed in the '523 patent is left on the patient's skin. Recognizing the side effects that can occur as a direct result of the time that the niacinamide remains in contact with the skin, the formulation disclosed in the '523 patent includes Aloe Vera extract and NaPCA. Aloe Vera extract has been found to have a direct effect in the treatment of acne as well as soothing qualities, and NaPCA acts as a moisturizer.

Topical application of niacinamide may often be beneficially combined with well known dermal cleansing techniques such as exfoliation. Human skin cells regularly die and are replaced with new cells. Exfoliation is a centuries-old process of removing the dead cells and excess accumulations of oil from the outermost layer of the skin. By removing the dead skin cells, the skin tends to look healthier and better—lighter,smoother and more evenly textured. Exfoliation may also help to unclog pores and stimulate hydration of the skin. The treatment outlined in the '523 patent recognizes the benefits of exfoliation and recommends that the area to be treated be scrubbed with an exfoliating scrub such as a conventional apricot scrub prior to application of the niacinamide-containing topical solution. In this process a standard exfoliating scrub is used to clean the skin. The scrub is then rinsed off and an aqueous liquid containing niacinamide is topically applied by spraying on the areas to be treated.

There are many different approaches to exfoliation. These include topically applied compounds that contain various acids such as hydroxy acids that dissolve the dead skin cells. The dead cells are washed off with the topically applied compounds. Another common method of exfoliation relies upon mechanical abrasion of the skin with heavy bristle brushes, scrubbers, loofas and the like. And yet another common method of exfoliating the skin is a combination of the two methods just mentioned in a topically applied exfoliating scrub that contains an abrasive material. Common abrasive materials included in such scrubs include ground apricot pits and walnut husks. These abrasive materials are generally delivered in a cream base. Exfoliation with these products involves application of the exfoliating agent to the skin, followed by gentle scrubbing and then cleansing to remove the exfoliating agent.

As noted above, niacinamide is known to have therapeutic benefits in the treatment of acne. However, traditional thinking has always been that the niacinamide had to be left on the skin for a significant period of time in order to be therapeutically effective. The present invention arises out of the unexpected and surprising results obtained by combining niacinamide into an appropriate carrier that also includes an abrasive compound to formulate an exfoliating scrub that is washed off immediately after use. Contrary to prior knowledge and the teachings of the prior art, the niacinamide included in the formulation of the present invention provides therapeutic benefits despite the fact that it is removed rapidly compared to prior topical application. By removing the active agent, niacinamide, from the skin immediately, the adverse reactions often associated with prolonged exposure to niacinamide are reduced or eliminated.

DETAILED DESCRIPTION OF PREFERRED EMBODIMENTS

The exfoliating scrub of the present invention is useful as a treatment for acne and other skin conditions. In its most preferred embodiment the present invention is a combination of an effective amount of niacinamide in a dermatologically inert viscous cream base that includes an effective amount of any suitable abrasive compound. The scrub is applied to the area to be treated and is lightly massaged into the skin, as with any exfoliating scrub. The scrub is then removed, preferably by washing with warm water. More particularly, the present invention is formulated with a combination of compounds that are combined in an aqueous phase. These ingredients are combined with various ingredients in an oil phase. Once heated, the aqueous phase and the oil phase are combined with any suitable abrasive agent and with niacinamide.

In the preferred embodiment of the present invention, the scrub comprises a viscous cream having a therapeutically effective amount of niacinamide in a pharmaceutically acceptable carrier that includes an effective amount of an exfoliating or abrading agent. The viscous cream acts as a carrier for the niacinamide and the abrading agent and may comprise any suitable cream, paste, gel or any similar carrier that is mild or inert to the skin. As used herein, the terms cream or scrub mean any suitable viscous carrier, including pourable liquids, pastes, gels and the like that suspend the exfoliating agent and in which the active agent niacinamide is contained. In the practice of the present invention about 1 to 20% concentration by weight of niacinamide is incorporated into a cream carrier that in addition contains an effective amount of an abrasive exfoliating agent. A preferred abrasive agent is walnut shell powder, which is added to the cream in an amount of about 5 to 7% concentration by weight. Walnut shell powder is a commercially available product that is made of ground walnut husks. It is a preferred exfoliant in the present invention because it is a natural ingredient that is known to be hypoallergenic. However, there are many well known abrasive agents that may be equivalently used in place of walnut shell powder. Moreover, those skilled in the art will further recognize that the present invention is effective with any of the other well known exfoliating techniques such as enzymatic or acidic agents, or mechanical abrading compounds or devices. For example, a cream carrier could incorporate any suitable exfoliating agent.

It has been found that this combination of ingredients in a suitable cream carrier is an effective therapeutic treatment for acne. The cream is applied to the affected area, typically the face, and is used in the same manner as other exfoliating scrubs by massaging the cream into the skin. The abrasive agent acts to remove dead skin cells and the niacinamide is brought into direct contact with the affected areas. The cream is then removed by washing the area with water, and if desired, a mild soap.

It has been unexpectedly been found that the niacinamide has a beneficial therapeutic effect on acne despite the fact that the cream is immediately removed. This was a surprising result because, as noted above, the traditional treatment of acne with niacinamide was to leave the agent in contact with the affected area to be treated for a significant period of time.

Although the cream of the present invention may include only the effective ingredients noted above, an exfoliating agent according to the present invention may optionally contain the additional compounds listed as follows in Table 1.

TABLE 1

| Ingredient | Concentration Range (weight percent) |
| --- | --- |
| A. Water | 50–60% |
| B. Sucrose cocoate | 3–6% |
| C. Disodium oleth-3 sulfosuccinate | 7.5–12.5% |
| D. Citric acid | 1–3% |
| E. Beta carotene | 0.01% |
| F. Apricot kernel oil | 2–4% |
| G. Cetyl alcohol | 4.5–8.5% |
| H. Walnut shell powder | 5–7% |
| I. Niacinamide | 1–20% |
| J. Sodium PCA | 0.25–1.25% |
| K. Aloe Vera extract | 0.25–1.25% |

An exfoliating cream according to the formulation of Table 1 is prepared by combining the aqueous phase compounds A through E from Table 1 and heating those ingredients to about 170° F. while mixing with sufficient agitation to completely blend all ingredients. The oil phase compounds F and G are likewise separately combined and heated to about 170° F. while mixing. The heated aqueous and oil phases are then combined and blended thoroughly with sufficient agitation to emulsify the two phases. The combination of ingredients A through G is then allowed to cool. When cooled, the remaining ingredients H through K are added and completely and homogeneously blended into the combined ingredients A through G, forming a cream.

In the formulation of table 1, citric acid is used as a preservative and for its antioxidant properties. Like the other ingredients listed in table 1, citric acid is useful because it is a natural product that is unlikely to cause adverse reactions. As noted above, a known side effect of exposure to niacinamide is stinging and dryness in some patients. Although the exfoliating cream is immediately removed from the skin, Aloe Vera extract is included in the formulation because it is known to be effective in reducing any stinging resulting from the niacinamide and is known to have directly beneficial effects in the treatment of acne. Sodium PCA (NaPCA), which is the sodium salt of pyrrolidone carboxylic acid, is included in the formulation of Table 1 as a natural moisturizer that minimizes drying.

In the formulation listed in Table 1 various substitutions may be made to make an equivalent product. For example, other exfoliating agents may be substituted for the walnut shell powder, including for example enzymatic agents known to have exfoliating effects and other exfoliants such as acidic compounds. Moreover, a scrub containing the therapeutically effective amounts of niacinamide described above, but omitting the exfoliating agent may be formulated. Such a scrub may be used in combination with a mechanical exfoliating agent such as a bristle brush or loofa or the like with equivalent results. Treatment with a cream that includes niacinamide but omits the exfoliating agent is accomplished by applying the cream to the skin and then exfoliating the area of skin with the mechanical exfoliating device. The cream is then removed as above, preferably by washing with warm water.

The cream of the present invention has been shown to be effective in reducing the number and severity of lesions resulting from acne and other skin conditions that cause blemishes. The frequency with which the exfoliating scrub is applied depends upon several factors, including the severity of the skin condition, and the user's skin type and sensitivity. Patients having oily skin may use the scrub as often as once to twice per day. Patients having dry skin or sensitive skin generally will use the scrub less often. The precise frequency is determined on a case by case basis influenced by the actual results achieved. As described above, the cream is topically applied to the area to be treated and is gently massaged into the skin. The cream is then immediately removed, preferably with warm water. The skin may beneficially be thoroughly cleansed prior to application of the cream of the present invention. In all cases the scrub is washed from the skin immediately after use.

While the present invention has been described in terms of a preferred embodiment, it will be appreciated by one of ordinary skill that the spirit and scope of the invention is not limited to those embodiments, but extend to the various modifications and equivalents as defined in the appended claims.

What is claimed is:

1. A method of treating acne comprising the steps of:

(a) applying topically to an area of skin to be treated a scrub containing a therapeutically effective amount of niacinamide;

(b) exfoliating said area;

(c) immediately after step (b), removing said scrub from said area.

2. The method of claim 1 wherein said scrub contains niacinamide in an amount between about 1 to 20% by weight.

3. The method of claim 1 wherein said scrub further contains an effective amount of an exfoliating agent and step (b) further comprises the step of massaging the scrub into the area of skin to be treated.

4. The method of claim 3 wherein said exfoliating agent comprises walnut shells contained in said scrub in an amount between about 5 to 7% by weight.

5. The method of claim 1 wherein step (b) further comprises abrading said area of skin with a mechanical abrading device.

6. The method of claim 3 wherein said exfoliating agent comprises an enzyme.

* * * * *